(12) United States Patent
Ma et al.

(10) Patent No.: US 9,668,890 B2
(45) Date of Patent: Jun. 6, 2017

(54) ANTI-THROMBOGENIC MEDICAL DEVICES AND METHODS

(71) Applicant: Covidien LP, Mansfield, MA (US)

(72) Inventors: Xiaodong Ma, Hudson, MA (US); Min-Shyan Sheu, Chelmsford, MA (US); Lincoln Eramo, Winchester, CA (US); John Wainwright, Rancho Santa Margarita, CA (US); Junwei Li, Irvine, CA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/087,459

(22) Filed: Nov. 22, 2013

(65) Prior Publication Data

US 2015/0148882 A1 May 28, 2015

(51) Int. Cl.
*A61F 2/82* (2013.01)
*A61L 31/02* (2006.01)
*A61L 31/10* (2006.01)
*A61L 31/16* (2006.01)
*A61F 2/90* (2013.01)

(52) U.S. Cl.
CPC .................. *A61F 2/82* (2013.01); *A61F 2/90* (2013.01); *A61L 31/022* (2013.01); *A61L 31/10* (2013.01); *A61L 31/16* (2013.01); *A61L 2300/42* (2013.01); *A61L 2400/18* (2013.01)

(58) Field of Classification Search
CPC ...... A61L 33/0076; A61L 27/40; A61L 31/12; A61L 2300/61; A61L 2420/04; A61F 2310/00149; A61F 2310/00059; A61F 2250/0015–2250/0021
USPC .................. 623/1.11–1.54, 23.72; 606/151; 427/2.24
See application file for complete search history.

(56) References Cited

U.S. PATENT DOCUMENTS

| | | |
|---|---|---|
| 5,624,411 A | 4/1997 | Tuch |
| 5,722,984 A | 3/1998 | Fischell et al. |
| 5,973,068 A | 10/1999 | Yamaya et al. |
| 6,048,910 A | 4/2000 | Furuya et al. |
| 6,156,373 A | 12/2000 | Zhong et al. |
| 6,322,847 B1 | 11/2001 | Zhong et al. |
| 6,461,735 B1 | 10/2002 | Furuya et al. |
| 7,077,860 B2 | 7/2006 | Yan et al. |

(Continued)

OTHER PUBLICATIONS

Troughton, Ernest B., et al., "Monolayer Films Prepared by the Spontaneous Self-Assembly of Symmetrical and Unsymmetrical Dialkyl Sulfides from Solution onto Gold Substrates: Structure, Properties, and Reactivity of Constituent Functional Groups", Langmuir, vol. 4, pp. 365-385 (1988).

(Continued)

*Primary Examiner* — Kathleen Holwerda
*Assistant Examiner* — Socrates L Boutsikaris
(74) *Attorney, Agent, or Firm* — Mark J. Kertz

(57) ABSTRACT

Methods for applying layers to medical devices and related devices are provided. Such devices can include stents. For example, the device can include a sidewall and a plurality of pores in the sidewall that are sized to inhibit flow of blood through the sidewall into an aneurysm to a degree sufficient to lead to thrombosis and healing of the aneurysm when the tubular member is positioned in a blood vessel and adjacent to the aneurysm. The device can have an anti-thrombogenic outer layer distributed over at least a portion of the device.

19 Claims, 2 Drawing Sheets

(56) References Cited

U.S. PATENT DOCUMENTS

| | | |
|---|---|---|
| 7,198,675 B2 | 4/2007 | Fox et al. |
| 7,258,891 B2 | 8/2007 | Pacetti et al. |
| 7,297,159 B2 | 11/2007 | Hossainy et al. |
| RE40,722 E | 6/2009 | Chappa |
| 7,553,377 B1 | 6/2009 | Chen et al. |
| 7,563,277 B2 | 7/2009 | Case et al. |
| 7,563,324 B1 | 7/2009 | Chen et al. |
| 7,572,336 B2 | 8/2009 | Van Sciver et al. |
| 7,588,642 B1 | 9/2009 | Morris et al. |
| 7,604,700 B2 | 10/2009 | Fox et al. |
| 7,622,070 B2 | 11/2009 | Atladottir et al. |
| 7,632,307 B2 | 12/2009 | Pacetti et al. |
| 7,648,725 B2 | 1/2010 | Van Sciver et al. |
| 7,669,548 B2 | 3/2010 | Chappa |
| 7,704,544 B2 | 4/2010 | Pacetti et al. |
| 7,735,449 B1 | 6/2010 | Harold et al. |
| 7,823,533 B2 | 11/2010 | Chen et al. |
| 7,833,544 B2 | 11/2010 | Lewis et al. |
| 7,939,095 B2 | 5/2011 | Zhao |
| 7,958,840 B2 | 6/2011 | Chappa |
| 7,959,942 B2 | 6/2011 | Cottone |
| 7,985,440 B2 | 7/2011 | Pacetti et al. |
| 7,985,441 B1 | 7/2011 | Tang et al. |
| 8,003,156 B2 | 8/2011 | Van Sciver |
| 8,069,814 B2 | 12/2011 | Guerriero et al. |
| 8,097,291 B2 | 1/2012 | Fredrickson et al. |
| 8,188,180 B2 | 5/2012 | Jonschker et al. |
| 8,197,879 B2 | 6/2012 | Fox et al. |
| 8,221,495 B2 | 7/2012 | Shrivastava et al. |
| 8,267,986 B2 | 9/2012 | Berez et al. |
| 8,273,101 B2 | 9/2012 | Garcia et al. |
| 8,308,699 B2 | 11/2012 | Zhang et al. |
| 8,591,566 B2 | 11/2013 | Newell et al. |
| 8,789,452 B1* | 7/2014 | Janardhan et al. ............... 87/9 |
| 2003/0033007 A1 | 2/2003 | Sirhan et al. |
| 2003/0050691 A1 | 3/2003 | Shifrin et al. |
| 2004/0185081 A1 | 9/2004 | Verlee et al. |
| 2004/0236399 A1* | 11/2004 | Sundar ..................... A61F 2/91 |
| | | 623/1.11 |
| 2004/0254634 A1 | 12/2004 | Verlee et al. |
| 2005/0015142 A1 | 1/2005 | Austin et al. |
| 2005/0022915 A1 | 2/2005 | Bowen et al. |
| 2005/0060028 A1 | 3/2005 | Horres et al. |
| 2005/0107869 A1 | 5/2005 | Sirhan et al. |
| 2005/0158449 A1 | 7/2005 | Chappa |
| 2005/0179011 A1 | 8/2005 | van Ooij et al. |
| 2006/0047336 A1 | 3/2006 | Gale et al. |
| 2006/0052757 A1 | 3/2006 | Fischer et al. |
| 2006/0088653 A1 | 4/2006 | Chappa |
| 2006/0177476 A1 | 8/2006 | Saffran |
| 2007/0003753 A1 | 1/2007 | Asgari |
| 2007/0043428 A1 | 2/2007 | Jennings et al. |
| 2007/0189915 A1 | 8/2007 | Shrivastava et al. |
| 2008/0033522 A1 | 2/2008 | Grewe et al. |
| 2008/0145393 A1 | 6/2008 | Trollsas et al. |
| 2008/0206829 A1* | 8/2008 | Yu ..................... A61B 5/14532 |
| | | 435/174 |
| 2009/0011117 A1 | 1/2009 | Nunez et al. |
| 2009/0155335 A1 | 6/2009 | O'Shaughnessey et al. |
| 2009/0254174 A1 | 10/2009 | Case et al. |
| 2010/0131044 A1* | 5/2010 | Patel ............................ 623/1.16 |
| 2010/0179644 A1 | 7/2010 | Jennings et al. |
| 2010/0226955 A1* | 9/2010 | Ludwig et al. ............... 424/423 |
| 2011/0000658 A1 | 1/2011 | Tanaka et al. |
| 2011/0027757 A1 | 2/2011 | Kyomoto et al. |
| 2011/0039013 A1 | 2/2011 | Papp et al. |
| 2011/0208294 A1 | 8/2011 | Cottone |
| 2012/0164458 A1 | 6/2012 | Biteau et al. |
| 2012/0197413 A1 | 8/2012 | Kyomoto et al. |
| 2013/0226276 A1 | 8/2013 | Newell et al. |
| 2013/0245745 A1* | 9/2013 | Vong ..................... A61F 2/885 |
| | | 623/1.12 |
| 2014/0277400 A1 | 9/2014 | Wainwright et al. |
| 2015/0066128 A1 | 3/2015 | Losordo et al. |
| 2015/0081003 A1 | 3/2015 | Wainwright et al. |
| 2015/0140344 A1 | 5/2015 | Ma et al. |

OTHER PUBLICATIONS

Fu, X., et al., "Surface Modification of Small Platinum Nanoclusters with Alkylamine and Alkylthiol: An XPS Study on the Influence of Organic Ligands on the Pt 4f Binding Energies of small Platinum Nanoclusters", Journal of Colloid and Interface Science, vol. 243, pp. 326-330 (2001).

Product description for Lipidure®-CM (MPC polymer) retrieved on Apr. 9, 2013 from http://nofamerica.net/store/index.php?dispatch=categories.view&category_id=146.

Product description for Lipidure®-PC (MPC monomer) retrieved on Apr. 9, 2013 from htip://nofamerica.net/store/index.php?dispatch=categories.view&category_id=145.

Product description Reactive MPC Polymers retrieved Apr. 9, 2013 from http://nofamerica.net/store/index.php?dispatch=categories.view&category_id=212.

U.S. Appl. No. 13/844,577, filed Mar. 15, 2013, John Wainwright.

U.S. Appl. No. 14/040,477, filed Sep. 27, 2013, Michael L. Losordo.

Extended European Search Report from Counterpart European Patent Application No. 14193763.1, dated Feb. 23, 2014, 7 pp.

International Preliminary Report on Patentability from International Application No. PCT/US2014/064930, mailed Jun. 2, 2016, 8 pp.

"A Guide to Silane Solutions from Dow Corning," Dow Corning Corporation, 2005, 32 pp. (Applicant points out that, in accordance with MPEP 609.04(a), the 2005 year of publication is sufficiently earlier than the effective U.S. filing date and any foreign priority date of Nov. 22, 2013 so that the particular month of publication is not in issue.).

"Silane Coupling Agents: Connecting Across Boundaries," Gelest, Inc., 2006, 60 pp. (Applicant points out that, in accordance with MPEP 609.04(a), the 2006 year of publication is sufficiently earlier than the effective U.S. filing date and any foreign priority date of Nov. 22, 2013 so that the particular month of publication is not in issue.).

Summary of Safety and Effectiveness Data, BiodivYsio AS PC (phosphorylcholine) Coated Stent Delivery System (BiodivYsio AS), Sep. 29, 2000, 26 pp.

"Summary of Safety and Effectiveness Data," Oct. 10, 2007, 59 pp.

Bridges et al., "Advances in drug eluting stents—focus on the Endeavor® zotarolimus stent," Medical Devices: Evidence and Research, Dec. 7, 2008, pp. 1-8.

Chen et al., "Surfaces having dual fibrinolytic and protein resistant properties by immobilization of lysine on polyurethane through a PEG spacer," Journal of Biomedical Materials Research Part A, Jul. 21, 2008, pp. 940-946.

Dumitriu, "Polymeric Biomaterials: Structure and Function," Table 25.6, CRC Press, Dec. 15, 2011, 1 pp.

Ehlers et al., "Theoretical Study on Mechanisms of the Epoxy-Amine Curing Reaction," Macromolecules, vol. 40, May 19, 2007, pp. 4370-4377.

Feng et al., "Atom-Transfer Radical Grafting Polymerization of 2-Methacryloyloxyethyl Phosphorylcholine from Silicon Wafer Surfaces," Journal of Polymer Science: Part A: Poymer Chemistry, vol. 42, Jan. 23, 2004, pp. 2931-2942.

Kang et al., "Fabrication of biofunctional stents with endothelial progenitor cell specificity for vascular re-endothelialization," Colloids and Surfaces B: Biointerfaces, vol. 102, Sep. 17, 2012, pp. 744-751.

Lee et al., "Covalent incorporation of starch derivative into waterborne polyurethane for biodegradability," Carbohydrate Polymers, vol. 87, Oct. 6, 2011, pp. 1803-1809.

Lewis et al., "Poly(2-methacryloyloxyethyl phosphorylcholine) for Protein Conjugation," Bioconjugate Chemistry, vol. 19, Sep. 19, 2008, pp. 2144-2155.

Lin et al., "Surface characterization and platelet adhesion studies on polyurethane surface immobilized with C60," Biomaterials, vol. 20, Mar. 31, 1999, pp. 1613-1620.

(56) References Cited

OTHER PUBLICATIONS

Love et al., "Self-Assembled Monolayers of Thiolates on Metals as a Form of Nanotechnology," Chem. Rev, vol. 105, Mar. 25, 2005, pp. 1103-1169.

Luzinov et al., "Epoxy-Terminated Self-Assembled Monolayers: Molecular Glues for Polymer Layers," Langmuir, vol. 16, Oct. 29, 1999, pp. 504-516.

McAuliffe et al., "Immediate and Midterm Results following Treatment of Recently Ruptured Intracranial Aneurysms with the Pipeline Embolization Device," AJNR Am J. Neuroradiol, vol. 33, Mar. 2012, pp. 487-493.

Ren et al., "Hemocompatibility Evaluation of Polyurethane Film with Surface-Grafted Poly(ethylene glycol) and Carboxymethyl-Chitosan," Journal of Applied Polymer Science, May 4, 2012, pp. 308-315.

Sanchis et al., "Surface Modification of a Polyurethane Film by Low Pressure Glow Discharge Oxygen Plasma Treatment," Journal of Applied Polymer Science, vol. 105, Apr. 9, 2007, pp. 1077-1085.

Sidouni et al., "Surface properties of a specifically modified high-grade medical polyurethane," Surface Science, vol. 491, Apr. 26, 2001, pp. 355-369.

Tsukruk et al., "Sticky Molecular Surfaces: Epoxysilane Self-Assembled Monolayers," Langmuir, vol. 15, Apr. 1, 1999, pp. 3029-3032.

Yakai et al., "Surface Modification of Polycarbonate Urethane by Covalent Linkage of Heparin with a PEG Spacer," Tianjin University and Springer-Verlag Berlin Heidelberg, vol. 19, Feb. 9, 2013, pp. 58-65.

Zhang et al., "Superlow Fouling Sulfobetaine and Carboxybetaine Polymers on Glass Slides," Langmuir, vol. 22, Oct. 28, 2006, pp. 10072-10077.

\* cited by examiner

ANTI-THROMBOGENIC MEDICAL DEVICES AND METHODS

BACKGROUND

Walls of the vasculature, particularly arterial walls, may develop areas of weakness and/or dilatation called aneurysms. The rupture of certain aneurysms, for example abdominal aortic aneurysms and brain or cerebral aneurysms in the neurovasculature, can cause hemorrhage and death. Aneurysms are generally treated by excluding the weakened part of the vessel from the arterial circulation. For treating a cerebral aneurysm, such exclusion may be accomplished by: (i) surgical clipping, where a metal clip is secured around the base of the aneurysm; (ii) packing the aneurysm with small, flexible wire coils (micro-coils); (iii) using embolic materials to "fill" an aneurysm; (iv) using detachable balloons or coils to occlude the parent vessel that supplies the aneurysm; and/or (v) intravascular stenting, including flow-diverter therapy.

Stents include generally tubular prostheses that expand radially or otherwise within a vessel or lumen to provide therapy or support against blockage of the vessel. Stents of various construction may be utilized, including balloon expandable metal stents, self-expanding braided metal stents, knitted metal stents, coiled stents, rolled stents, and the like. Stent-grafts are also used, which include a tubular graft material supported by a metallic stent.

Coatings have been applied to medical devices to impart lubricious and/or anti-adhesive properties and serve as depots for bioactive agent release. As medical devices, especially those possessing irregular and/or rough surfaces, may be conducive to thrombus formation, coatings may be applied to these medical devices to reduce the formation of thrombi. Adherence of these coatings to the substrate used to form the device may prove difficult, with delamination occurring in some cases.

SUMMARY

In accordance with certain embodiments in the present disclosure, a medical device (e.g., a stent) is provided having outer layer(s) thereon that provide the device with reduced thrombogenicity. In embodiments, a medical device of the present disclosure includes an expandable tubular body having a plurality of braided filaments configured to be implanted in a blood vessel, the braided filaments including a metal such as platinum, cobalt, chromium, nickel, alloys thereof, and combinations thereof; wherein the filaments have an outer surface including a phosphorylcholine; and wherein the phosphorylcholine has a thickness of less than 100 nanometers.

Systems using the medical devices of the present disclosure are also provided. In embodiments, a system of the present disclosure includes a system for treating an aneurysm. Such a system includes a core assembly configured for insertion into a blood vessel, the core assembly having a distal segment; an expandable tubular body carried by the core assembly distal segment, the tubular body having a plurality of braided filaments configured to be implanted in a blood vessel, the braided filaments including a metal such as platinum, cobalt, chromium, nickel, alloys thereof, and combinations thereof; wherein the filaments have an outer surface including a phosphorylcholine; and wherein the phosphorylcholine has a thickness of less than 100 nanometers.

Methods for treating medical conditions with the devices of the present disclosure are also provided. In embodiments, a method of the present disclosure includes a method of treating an aneurysm formed in a wall of a parent blood vessel. Such a method includes deploying the tubular body of a medical device of the present disclosure into the parent blood vessel so that a sidewall of the medical device extends across a neck of the aneurysm, thereby causing thrombosis within the aneurysm.

In other embodiments, a method of treating an aneurysm formed in a wall of a parent blood vessel of a patient includes deploying a flow-diverting metallic stent having a phosphorylcholine outer surface of less than 100 nanometers in thickness in the parent blood vessel across the neck of the aneurysm, so as to treat the aneurysm; and either (a) prescribing to the patient a reduced protocol of anti-platelet medication, in comparison to a protocol that would be prescribed to the patient if an otherwise similar stent that lacks the phosphorylcholine outer surface were deployed in the patient, or (b) declining to prescribe to the patient any anti-platelet medication.

In yet other embodiments, a method of treating an aneurysm formed in a wall of a parent blood vessel of a patient includes deploying a flow-diverting stent in the parent blood vessel across the neck of the aneurysm, so as to treat the aneurysm, at least a portion of the stent having a phosphorylcholine outer surface of less than 100 nanometers in thickness so that the stent exhibits a peak thrombin concentration that is less than 0.8 times the peak thrombin concentration of an otherwise similar stent that lacks the phosphorylcholine outer surface; and either (a) prescribing to the patient a reduced protocol of anti-platelet medication, in comparison to a protocol that would be prescribed to the patient if the otherwise similar stent that lacks the phosphorylcholine outer surface were deployed in the patient, or (b) declining to prescribe to the patient any anti-platelet medication.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 5. The other clauses can be presented in a similar manner.

Clause 1. A medical device, comprising:
an expandable tubular body comprising a plurality of braided filaments configured to be implanted in a blood vessel, the braided filaments comprising a metal selected from the group consisting of platinum, cobalt, chromium, nickel, alloys thereof, and combinations thereof;
wherein the filaments have an outer surface comprising a phosphorylcholine; and
wherein the phosphorylcholine has a thickness of less than 100 nanometers.

Clause 2. The medical device of Clause 1, wherein the phosphorylcholine is selected from the group consisting of 2-methacryloyloxyethyl phosphorylcholine, 2-acryloyloxyethyl phosphorylcholine, and phosphorylcholines based upon monomers such as 2-(meth)acryloyloxyethyl-2'-(trimethylammonio)ethyl phosphate, 3-(meth)acryloyloxypropyl-2'-(trimethylammonio)ethyl phosphate, 4-(meth)acryloyloxybutyl-2'-(trimethylammonio)ethyl phosphate, 5-(meth)acryloyloxypentyl-2'-(trimethylammonio)ethyl phosphate, 6-(meth)acryloyloxyhexyl-2'-(trimethylammonio)ethyl phosphate, 2-(meth)acryloyloxyethyl-2'-(triethylammonio)ethyl phosphate, 2-(meth)acryloyloxyethyl-2'-(tripropylammonio)ethyl phosphate, 2-(meth)acryloyloxyethyl-2'-(tributylammonio)ethyl phosphate, 2-(meth)acryloyloxypropyl-2'-(trimethylammonio)ethyl phosphate, 2-(meth)acryloyloxybutyl-2'-(trimethylammonio)ethyl phosphate, 2-(meth)acryloyloxypentyl-2'-(trimethylammonio)ethyl phosphate, 2-(meth)acryloyloxyhexyl-2'-(trimethylammonio)ethyl phosphate, 2-(meth)acryloyloxyethyl-3'-(trimethylammonio)propyl phosphate, 3-(meth)acryloyloxypropyl-3'-(trimethylammonio)propyl phosphate, 4-(meth)acryloyloxybutyl-3'-(trimethylammonio)propyl phosphate, 5-(meth)acryloyloxypentyl-3'-(trimethylammonio)propyl phosphate, 6-(meth)acryloyloxyhexyl-3'-(trimethylammonio)propyl phosphate, 2-(meth)acryloyloxyethyl-4-(trimethylammonio)butyl phosphate, 3-(meth)acryloyloxypropyl-4'-(trimethylammonio)butyl phosphate, 4-(meth)acryloyloxybutyl-4'-(trimethylammonio)butyl phosphate, 5-(meth)acryloyloxypentyl-4'-(trimethylammonio)butyl phosphate, 6-(meth)acryloyloxyhexyl-4'-(trimethylammonio)butylphosphate, and combinations thereof.

Clause 3. The medical device of Clause 1, wherein the phosphorylcholine comprises a copolymer having a reactive chemical group.

Clause 4. The medical device of Clause 3, wherein the reactive chemical group is selected from the group consisting of amine, hydroxyl, epoxy, silane, aldehyde, carboxylate and thiol.

Clause 5. The medical device of Clause 1, further comprising a silane layer between the metal and the phosphorylcholine.

Clause 6. The medical device of Clause 5, wherein the silane is selected from the group consisting of 3-glycidoxypropyltrimethoxysilane, 2-(3,4-epoxycyclohexyl)ethyl-triethoxysilane, 2-(3,4-epoxycyclohexyl)ethyl-trimethoxysilane, (3-glycidoxypropyl)trimethoxysilane, (3-glycidoxypropyl)triethoxysilane, 5,6-epoxyhexyltriethoxysilane, (3-glycidoxypropyl)methyldiethoxysilane, (3-glycidoxypropyl)methyldimethoxysilane, (3-glycidoxypropyl)dimethylethoxysilane, 3-isocyanatopropyltriethoxysilane, (isocyanatomethyl)methyldimethoxysilane, 3-isocyanatopropyltrimethoxysilane, tris(3-trimethoxysilylpropyeisocyanurate, (3-triethoxysilylpropyl)-t-butylcarbamate, triethoxysilylpropylethylcarbamate, 3-thiocyanatopropyltriethoxysilane, and combinations thereof.

Clause 7. The medical device of Clause 1, wherein the tubular body comprises (a) platinum or platinum alloy filaments, combined with (b) cobalt-chromium alloy filaments.

Clause 8. The medical device of Clause 7, wherein the platinum or platinum alloy filaments possess a layer of the phosphorylcholine, and wherein the cobalt-chromium alloy filaments possess a silane intermediate layer between the cobalt-chromium alloy filaments and the phosphorylcholine.

Clause 9. The medical device of Clause 7, wherein the phosphorylcholine, or a polymer or copolymer thereof, is chemically bonded directly to the platinum or platinum alloy filaments.

Clause 10. The medical device of Clause 7, wherein the phosphorylcholine, or a polymer or copolymer thereof, is covalently bonded to the platinum or platinum alloy filaments.

Clause 11. The medical device of Clause 7, wherein the phosphorylcholine, or a polymer or copolymer thereof, is chemically bonded to a silane over the cobalt-chromium alloy filaments.

Clause 12. The medical device of Clause 11, wherein the phosphorylcholine, or the polymer or copolymer thereof, is covalently bonded to a silane over the cobalt-chromium alloy filaments.

Clause 13. The medical device of Clause 1, wherein the tubular body comprises platinum or platinum alloy filaments.

Clause 14. The medical device of Clause 13, wherein the phosphorylcholine, or a polymer or copolymer thereof, is covalently bonded to the platinum or platinum alloy filaments.

Clause 15. The medical device of Clause 13, wherein the phosphorylcholine, or a polymer or copolymer thereof, is chemically bonded to the platinum or platinum alloy filaments.

Clause 16. The medical device of Clause 1, wherein the tubular body has a sidewall formed by the braided filaments, the sidewall having a plurality of pores therein, the plurality of pores being sized to inhibit flow of blood through the sidewall into an aneurysm to a degree sufficient to lead to thrombosis and healing of the aneurysm when the tubular body is positioned in a blood vessel and adjacent to the aneurysm.

Clause 17. The medical device of Clause 1, wherein the tubular body has a sidewall formed by the braided filaments, the sidewall having a plurality of pores therein, the plurality of pores having an average pore size that is less than or equal to 500 microns.

Clause 18. The medical device of Clause 1, wherein the tubular body is heat set so that the filaments are at their least-stressed configuration in the tubular body.

Clause 19. The medical device of Clause 1, wherein the outer surface is an outermost surface of the filaments.

Clause 20. The medical device of Clause 1, wherein the medical device comprises a stent.

Clause 21. The medical device of Clause 1, wherein the phosphorylcholine has a thickness from about 1 to about 100 nanometers.

Clause 22. The medical device of Clause 1, wherein the tubular body is self-expanding.

Clause 23. The medical device of Clause 1, wherein the device is less thrombogenic than an identical device whose braided filaments are entirely bare metal.

Clause 24. The medical device of Clause 1, wherein the device exhibits an elapsed time before peak thrombin formation that is at least 1.5 times the elapsed time before peak thrombin formation for an identical device whose braided filaments are entirely bare metal.

Clause 25. The medical device of Clause 1, wherein the device exhibits a peak thrombin concentration that is less than 0.8 times the peak thrombin concentration for an identical device whose braided filaments are entirely bare metal.

Clause 26. A system for treating an aneurysm, the system comprising:
  a core assembly configured for insertion into a blood vessel, the core assembly having a distal segment;
  an expandable tubular body carried by the core assembly distal segment, the tubular body comprising a plurality of braided filaments configured to be implanted in a blood vessel, the braided filaments comprising a metal selected from the group consisting of platinum, cobalt, chromium, nickel, alloys thereof, and combinations thereof;

wherein the filaments have an outer surface comprising a phosphorylcholine; and wherein the phosphorylcholine has a thickness of less than 100 nanometers.

Clause 27. The system of Clause 26, wherein the phosphorylcholine is selected from the group consisting of 2-methacryloyloxyethyl phosphorylcholine, 2-acryloyloxyethyl phosphorylcholine, and phosphorylcholines based upon monomers such as 2-(meth)acryloyloxyethyl-2'-(trimethylammonio)ethyl phosphate, 3-(meth)acryloyloxypropyl-2'-(trimethylammonio)ethyl phosphate, 4-(meth)acryloyloxybutyl-2'-(trimethylammonio)ethyl phosphate, 5-(meth)acryloyloxypentyl-2'-(trimethylammonio)ethyl phosphate, 6-(meth)acryloyloxyhexyl-2'-(trimethylammonio)ethyl phosphate, 2-(meth)acryloyloxyethyl-2'-(triethylammonio)ethyl phosphate, 2-(meth)acryloyloxyethyl-2'-(tripropylammonio)ethyl phosphate, 2-(meth)acryloyloxyethyl-2'-(tributylammonio)ethyl phosphate, 2-(meth)acryloyloxypropyl-2'-(trimethylammonio)ethyl phosphate, 2-(meth)acryloyloxybutyl-2'-(trimethylammonio)ethyl phosphate, 2-(meth)acryloyloxypentyl-2'-(trimethylammonio)ethyl phosphate, 2-(meth)acryloyloxyhexyl-2'-(trimethylammonio)ethyl phosphate, 2-(meth)acryloyloxyethyl-3'-(trimethylammonio)propyl phosphate, 3-(meth)acryloyloxypropyl-3'-(trimethylammonio)propyl phosphate, 4-(meth)acryloyloxybutyl-3'-(trimethylammonio)propyl phosphate, 5-(meth)acryloyloxypentyl-3'-(trimethylammonio)propyl phosphate, 6-(meth)acryloyloxyhexyl-3'-(trimethylammonio)propyl phosphate, 2-(meth)acryloyloxyethyl-4'-(trimethylammonio)butyl phosphate, 3-(meth)acryloyloxypropyl-4'-(trimethylammonio)butyl phosphate, 4-(meth)acryloyloxybutyl-4'-(trimethylammonio)butyl phosphate, 5-(meth)acryloyloxypentyl-4'-(trimethylammonio)butyl phosphate, 6-(meth)acryloyloxyhexyl-4'-(trimethylammonio)butylphosphate, and combinations thereof.

Clause 28. The system of Clause 26, further comprising a silane layer between the metal and the phosphorylcholine.

Clause 29. The system of Clause 28, wherein the silane is selected from the group consisting of 3-glycidoxypropyltrimethoxysilane, 2-(3,4-epoxycyclohexyl)ethyl-triethoxysilane, 2-(3,4-epoxycyclohexyl)ethyl-trimethoxysilane, (3-glycidoxypropyl)trimethoxysilane, (3-glycidoxypropyl)triethoxysilane, 5,6-epoxyhexyltriethoxysilane, (3-glycidoxypropyl)methyldiethoxysilane, (3-glycidoxypropyl)methyldimethoxysilane, (3-glycidoxypropyl)dimethylethoxysilane, 3-isocyanatopropyltriethoxysilane, (isocyanatomethyl)methyldimethoxysilane, 3-isocyanatopropyltrimethoxysilane, tris(3-trimethoxysilylpropyl)isocyanurate, (3-triethoxysilylpropyl)-t-butylcarbamate, triethoxysilylpropylethylcarbamate, 3-thiocyanatopropyltriethoxysilane, and combinations thereof.

Clause 30. The system of Clause 26, wherein the tubular body comprises (a) platinum or platinum alloy filaments, combined with (b) cobalt-chromium alloy filaments.

Clause 31. The system of Clause 30, wherein the platinum or platinum alloy filaments possess a layer of the phosphorylcholine, and wherein the cobalt-chromium alloy filaments possess a silane intermediate layer between the cobalt-chromium alloy filaments and the phosphorylcholine.

Clause 32. The system of Clause 30, wherein the phosphorylcholine is chemically bonded directly to the platinum or platinum alloy filaments.

Clause 33. The system of Clause 30, wherein the phosphorylcholine is covalently bonded to the platinum or platinum alloy filaments.

Clause 34. The system of Clause 30, wherein the phosphorylcholine is chemically bonded to a silane over the cobalt-chromium alloy filaments.

Clause 35. The system of Clause 34, wherein the phosphorylcholine is covalently bonded to a silane over the cobalt-chromium alloy filaments.

Clause 36. The system of Clause 26, wherein the tubular body comprises platinum or platinum alloy filaments.

Clause 37. The system of Clause 36, wherein the phosphorylcholine is covalently bonded to the platinum or platinum alloy filaments.

Clause 38. The system of Clause 36, wherein the phosphorylcholine is chemically bonded to the platinum or platinum alloy filaments.

Clause 39. The system of Clause 26, wherein the tubular body has a sidewall formed by the braided filaments, the sidewall having a plurality of pores therein, the plurality of pores being sized to inhibit flow of blood through the sidewall into an aneurysm to a degree sufficient to lead to thrombosis and healing of the aneurysm when the tubular body is positioned in a blood vessel and adjacent to the aneurysm.

Clause 40. The system of Clause 26, wherein the tubular body has a sidewall formed by the braided filaments, the sidewall having a plurality of pores therein, the plurality of pores having an average pore size that is less than or equal to 500 microns.

Clause 41. The system of Clause 26, wherein the tubular body is heat set so that the filaments are at their least-stressed configuration in the tubular body.

Clause 42. The system of Clause 26, wherein the outer surface is an outermost surface of the filaments.

Clause 43. The system of Clause 26, wherein the tubular body comprises a stent.

Clause 44. The system of Clause 26, wherein the phosphorylcholine has a thickness from about 1 to about 100 nanometers.

Clause 45. The system of Clause 26, wherein the tubular body is self-expanding.

Clause 46. The system of Clause 26, wherein the tubular body is less thrombogenic than an identical body whose braided filaments are entirely bare metal.

Clause 47. The system of Clause 26, wherein the tubular body exhibits an elapsed time before peak thrombin formation that is at least 1.5 times the elapsed time before peak thrombin formation for an identical tubular body whose braided filaments are entirely bare metal.

Clause 48. The system of Clause 26, wherein the tubular body exhibits a peak thrombin concentration that is less than 0.8 times the peak thrombin concentration for an identical tubular body whose braided filaments are entirely bare metal.

Clause 49. The system of Clause 26, further comprising a microcatheter configured to slidably receive the core assembly and tubular member in a lumen of the microcatheter.

Clause 50. A method of treating an aneurysm formed in a wall of a parent blood vessel, the method comprising:
deploying the tubular body of any preceding Clause into the parent blood vessel so that a sidewall of the medical device extends across a neck of the aneurysm, thereby causing thrombosis within the aneurysm.

Clause 51. A method of treating an aneurysm formed in a wall of a parent blood vessel of a patient, the method comprising:

deploying a flow-diverting metallic stent having a phosphorylcholine outer surface of less than 100 nanometers in thickness in the parent blood vessel across the neck of the aneurysm, so as to treat the aneurysm; and
either (a) prescribing to the patient a reduced protocol of anti-platelet medication, in comparison to a protocol that would be prescribed to the patient if an otherwise similar stent that lacks the phosphorylcholine outer surface were deployed in the patient, or (b) declining to prescribe to the patient any anti-platelet medication.

Clause 52. The method of Clause 51, wherein the stent comprises the tubular body of any preceding Clause.

Clause 53. The method of Clause 51, wherein the patient is one who has been diagnosed as being at risk of an intracranial hemorrhage.

Clause 54. The method of Clause 51, wherein the patient is one who has been diagnosed as being at risk of a cerebral hemorrhage from an aneurysm.

Clause 55. The method of Clause 51, wherein the parent blood vessel is an intracranial artery.

Clause 56. The method of Clause 51, further comprising accessing a treatment region near the aneurysm by inserting a microcatheter into the parent vessel, and delivering the stent through the microcatheter to the treatment region.

Clause 57. The method of Clause 51, wherein the stent exhibits an elapsed time before peak thrombin formation that is at least 1.5 times the elapsed time of a similar stent that lacks the phosphorylcholine outer surface.

Clause 58. The method of Clause 51, wherein the stent exhibits a peak thrombin concentration that is less than 0.8 times the peak thrombin concentration for a similar stent that lacks the phosphorylcholine outer surface.

Clause 59. A method of treating an aneurysm formed in a wall of a parent blood vessel of a patient, the method comprising:
deploying a flow-diverting stent in the parent blood vessel across the neck of the aneurysm, so as to treat the aneurysm, at least a portion of the stent having a phosphorylcholine outer surface of less than 100 nanometers in thickness so that the stent exhibits a peak thrombin concentration that is less than 0.8 times the peak thrombin concentration of an otherwise similar stent that lacks the phosphorylcholine outer surface; and
either (a) prescribing to the patient a reduced protocol of anti-platelet medication, in comparison to a protocol that would be prescribed to the patient if the otherwise similar stent that lacks the phosphorylcholine outer surface were deployed in the patient, or (b) declining to prescribe to the patient any anti-platelet medication.

Clause 60. The method of Clause 59, wherein the stent comprises the tubular body of any preceding Clause.

Clause 61. The method of Clause 59, wherein the patient is one who has been diagnosed as being at risk of an intracranial hemorrhage.

Clause 62. The method of Clause 59, wherein the patient is one who has been diagnosed as being at risk of a cerebral hemorrhage from an aneurysm.

Clause 63. The method of Clause 59, wherein the parent blood vessel is an intracranial artery.

Clause 64. The method of Clause 59, further comprising accessing a treatment region near the aneurysm by inserting a microcatheter into the parent vessel, and delivering the stent through the microcatheter to the treatment region.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

The accompanying drawings, which are included to provide further understanding of the subject technology and are incorporated in and constitute a part of this specification, illustrate aspects of the disclosure and together with the description serve to explain the principles of the subject technology.

DETAILED DESCRIPTION

Figure 1:
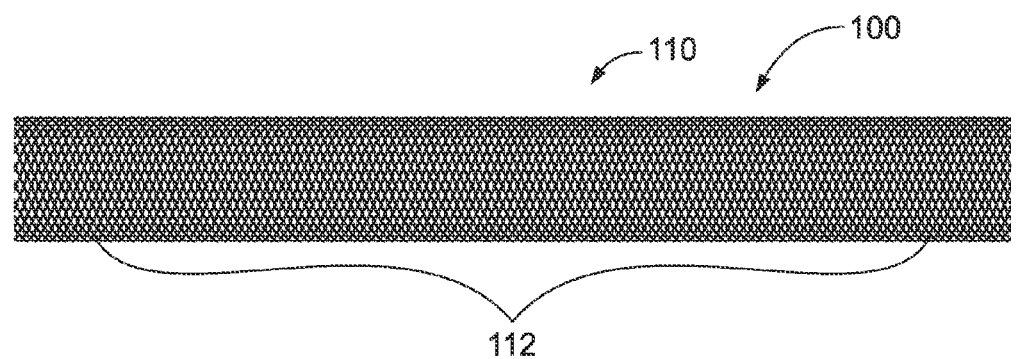
FIG. 1 is a side view of a stent including an outer layer thereon, according to some embodiments.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology. Further, although the present disclosure may refer to embodiments in which the apparatus is a stent, aspects of the embodiments disclosed herein can be used with any implantable device, such as coils, filters, scaffolds, ventricular assist devices, self-expanding and balloon-expandable stents, and other devices.

The present disclosure provides devices having coatings, surface treatments and/or layers thereon, as well as embodiments for applying coatings/surface treatments/layers to medical devices. Substrates used to form medical devices in accordance with the present disclosure may be formed of any suitable substance, including inert materials such as metals, glass, ceramics, combinations thereof, and the like.

In embodiments, substrates of the present disclosure may be formed of inert materials such as glass, ceramics, and/or metals. Suitable metals include gold, silver, copper, steel, aluminum, titanium, cobalt, chromium, platinum, nickel, alloys thereof, combinations thereof, and the like. Suitable alloys include nickel-titanium (e.g., nitinol), cobalt-nickel, cobalt-chromium, and platinum-tungsten. One suitable cobalt based alloy is 35N LT™ available from Fort Wayne Metals of Fort Wayne, Ind., USA.

In accordance with some embodiments disclosed herein, a medical device (e.g., stent) is provided that has reduced thrombogenicity. Further, in some embodiments, such a device can be braided and/or have a flow diverting section.

The medical devices of the present disclosure can include one or more polymer layers thereon. In embodiments, the present disclosure provides for the use of silanes to form an optional intermediate layer which binds to the substrate. In embodiments, polymer layers, layers of bioactive agents, combinations thereof, and the like, may then be applied to and bound directly to the substrate and/or any intermediate silane layer.

Silanes which may be utilized in forming the optional silane layer may have at least one functional group including, but not limited to, acrylate, methacrylate, aldehyde, amino, epoxy, ester, combinations thereof, and the like. In embodiments, additional silanes which may be used in forming the silane layer include, but are not limited to, 3-glycidyloxypropyl trimethoxysilane (GPTS), 2-(3,4-epoxycyclohexypethyl-triethoxysilane, epoxycyclohexyl) ethyl-trimethoxysilane, (3-glycidoxypropyl)trimethoxysilane, glycidoxypropyl)triethoxysilane, 5,6-epoxyhexyltriethoxysilane, (3-glycidoxypropyl) methyldiethoxysilane, (3-glycidoxypropyl) methyldimethoxysilane, (3-glycidoxypropyl) dimethylethoxysilane, 3-isocyanatopropyltriethoxysilane, (isocyanatomethyl)methyldimethoxysilane, 3-isocyanatopropyltrimethoxysilane, tris(3-trimethoxysilylpropyl)isocyanurate, (3-triethoxysilylpropyl)-t-butylcarbamate, triethoxysilylpropylethylcarbamate, 3-thiocyanatopropyltriethoxysilane, combinations thereof, and the like.

In embodiments, the silanes used to form the silane layer may be in solution, which is then applied to the substrate. Suitable solvents for forming the solution include, for example, ethanol, toluene, water, deionized water, methanol, isopropyl alcohol, n-butanol, dimethylformamide (DMF), dimethyl sulfoxide (DMSO), ethyl acetate, propylene glycol monomethyl ether acetate (PM acetate), toluene, chloroform, dichloromethane, combinations thereof, and the like. The solvents may be present in amounts from about 0.1% to about 99.9% by weight of the solution, in embodiments from about 50% to about 99.8% by weight of the solution. In some embodiments, the solution may include ethanol and water at a ratio from about 95%/5%. The silane may be in solution at a concentration from about 0.1% to about 99.9%, in embodiments from about 0.2% to about 50%.

In embodiments, a suitable solution for applying a silane layer may include GPTS in 95%/5% ethanol/water.

To apply the polymer layer and/or optional silane layer to the substrate, it may be desirable to first clean the substrate surface. For example, the substrate surface may first be subjected to sonication and cleaned with a suitable solvent such as acetone, isopropyl alcohol, ethanol, methanol, combinations thereof, and the like. Sonication may occur for a period of time from about 1 minute to about 20 minutes, in embodiments from about 5 minutes to about 15 minutes. However, in embodiments, sonication may occur for longer periods, up to 1 hour, up to 2 hours, or more than 2 hours. The solvents used in the sonication/cleaning may be applied as mixtures, or individual solvents may be applied sequentially, one or more times. The sonication may occur at room temperature, e.g. at about 21° C., or at temperatures from about 18° C. to about 55° C., in embodiments from about 40° C. to about 50° C., in embodiments about 45° C.

After cleaning, the substrates may be subjected to a treatment to enhance the formation of hydroxyl groups (sometimes referred to, herein, as hydroxylation). The surface of the substrate may be hydroxylated by subjecting the surface to a treatment with sodium hydroxide, nitric acid, sulfuric acid, hydrochloric acid, ammonium hydroxide, hydrogen peroxide, tert-butyl hydroperoxide, potassium dichromate, perchloric acid, oxygen plasma, water plasma, corona discharge, ozone, UV, combinations thereof, and the like. The material used for hydroxylation may be at a concentration from about 10% to about 100%, in embodiments from about 15% to about 25%, in embodiments about 20%. Hydroxylation may occur over a period of, time from about 0.5 hours to about 2.5 hours, or more than 2.5 hours, in embodiments from about 1 hour to about 2 hours, in embodiments about 1.5 hours, at room temperature. Hydroxylation may also occur with shaking from about 100 to about 160 revolutions per minute (rpm), in embodiments from about 120 to about 140 rpm, in embodiments about 130 rpm.

After hydroxylation, the substrate may be rinsed with a suitable material, such as deionized water, ethanol, methanol, combinations thereof, and the like.

The hydroxylated substrate may then be treated with the polymer and/or silanes described above. For example, in embodiments, the substrate may be immersed in a solution including the silane for a period of time from about 0.5 hours to about 3.5 hours, in embodiments from about 1 hour to about 3 hours, in embodiments for about 2 hours, at room temperature.

The silane solution possessing the substrate may also be subjected to shaking at a rate from about 100 to about 160 revolutions per minute (rpm), in embodiments from about 120 to about 140 rpm, in embodiments about 130 rpm.

After immersion in the silane materials, the substrate may then be dipped in, or sprayed with, a suitable material, such as ethanol, toluene, deionized water, methanol, isopropyl alcohol, n-butanol, dimethylformamide (DMF), dimethyl sulfoxide (DMSO), ethyl acetate, PM acetate, toluene, chloroform, dichloromethane, combinations thereof, and the like, from one time to about 5 times, in embodiments about 3 times. The substrate with the silanes thereon may then be heated at a temperature from about 30° C. to about 150° C., in embodiments from about 70° C. to about 90° C., in embodiments about 80° C. Heating may occur for a time from about 5 minutes to about 25 minutes, or more than 25 minutes, in embodiments from about 10 minutes to about 20 minutes, in embodiments about 15 minutes.

Where applied to a substrate, the silane layer may have a thickness less than 50 nanometers, or less than 20 nanometers, or less than 10 nanometers, in embodiments from about 1 nanometer to about 10 nanometers.

Once the optional silane layer has been formed, the medical device may be treated with additional components to form an outer layer on the silane layer. For example, bioactive agents may bind to free functional groups of the silane layer. Similarly, polymeric and/or monomeric materials may bind free functional groups on the substrate and/or optional silane layer, with or without bioactive agents.

Suitable polymeric and/or monomeric materials which may be utilized to form an outer layer on the medical device of the present disclosure, binding to either the substrate, the optional silane layer described above, or both, include any material suitable for use in the medical device. Such materials may provide desirable properties to the medical device, including reduced thrombogenicity, lubricity, drug delivery, protein or DNA delivery, prevention of restenosis, cell and protein adhesion, lubricity, RNA and/or gene delivery, antimicrobial, non-fouling, promoting endothelialization, combinations thereof, and the like.

In embodiments, suitable polymeric and/or monomeric materials which may bind to the substrate and/or optional silane layer, and be used to form an outer layer on the medical device of the present disclosure, include phosphorylcholines. Suitable phosphorylcholines include 2-methacryloyloxyethyl phosphorylcholine (MPC), 2-acryloyloxyethyl phosphorylcholine, and the like, and combinations thereof. Other phosphorylcholines may be utilized, including phosphorylcholines based upon monomers including, but not limited to, 2-(meth)acryloyloxyethyl-2'-(trimethylammonio)ethyl phosphate, 3-(meth)acryloyloxypropyl-2'-

(trimethylammonio)ethyl phosphate, 4-(meth)acryloyloxybutyl-2'-(trimethylammonio)ethyl phosphate, 5-(meth)acryloyloxypentyl-2'-(trimethylammonio)ethyl phosphate, 6-(meth)acryloyloxyhexyl-2'-(trimethylammonio)ethyl phosphate, 2-(meth)acryloyloxyethyl-2'-(triethylammonio) ethyl phosphate, 2-(meth)acryloyloxyethyl-2'-(tripropylammonio)ethyl phosphate, 2-(meth)acryloyloxyethyl-2'-(tributylammonio)ethyl phosphate, 2-(meth)acryloyloxypropyl-2'-(trimethylammonio)ethyl phosphate, 2-(meth)acryloyloxybutyl-2'-(trimethylammonio)ethyl phosphate, 2-(meth)acryloyloxypentyl-2'-(trimethylammonio)ethyl phosphate, 2-(meth)acryloyloxyhexyl-2'-(trimethylammonio)ethyl phosphate, 2-(meth)acryloyloxyethyl-3'-(trimethylammonio)propyl phosphate, 3-(meth)acryloyloxypropyl-3'-(trimethylammonio)propyl phosphate, 4-(meth)acryloyloxybutyl-3'-(trimethylammonio)propyl phosphate, 5-(meth)acryloyloxypentyl-3'-(trimethylammonio)propyl phosphate, 6-(meth)acryloyloxyhexyl-3'-(trimethylammonio)propyl phosphate, 2-(meth)acryloyloxyethyl-4'-(trimethylammonio)butyl phosphate, 3-(meth)acryloyloxypropyl-4'-(trimethylammonio)butyl phosphate, 4-(meth)acryloyloxybutyl-4'-(trimethylammonio)butyl phosphate, 5-(meth)acryloyloxypentyl-4'-(trimethylammonio)butyl phosphate, 6-(meth)acryloyloxyhexyl-4'-(trimethylammonio)butylphosphate, and combinations thereof. As used herein, "(meth)acryl" includes both methacryl and/or acryl groups. Such phosphorylcholines include those commercially available as LIPIDURE® MPCs (including for example LIPIDURE®-NH01, a reactive MPC) from NOF Corporation of Tokyo, Japan. Phosphorylcholines can include reactive phosphorylcholines, for example in the form of a copolymer of phosphorylcholine and a reactive chemical group. The reactive group can be, for example, amine, hydroxyl, epoxy, silane, aldehyde, carboxylate or thiol.

In embodiments, the phosphorylcholines used to form the polymer layer may be in solution, which is then applied to the substrate and/or optional silane layer. Suitable solvents for forming the solution possessing the polymer, such as the above phosphorylcholines, include, for example, ethanol, water, deionized water, methanol, isopropyl alcohol, n-butanol, dimethylformamide (DMF), dimethyl sulfoxide (DMSO), ethyl acetate, PM acetate, toluene, chloroform, dichloromethane, combinations thereof, and the like. The polymer may be present in amounts from about 0.5% to about 95% by weight of the solution, in embodiments from about 1% to about 50% by weight of the solution. In some embodiments, the solution may include MPC at a concentration of about 5%.

The polymer may be applied to the substrate and/or optional silane layer using various methods, including dipping, spraying, brushing, combinations thereof, and the like. For example, in embodiments, a substrate, optionally possessing a silane layer, may be immersed in a solution including the polymer for a period of time from about 30 seconds to about 90 seconds, in embodiments from about 45 seconds to about 75 seconds, in embodiments for about 45 seconds, at room temperature. Additional information on polymer application methods may be found in U.S. patent application Ser. No. 13/844,577, filed Mar. 15, 2013, titled COATED MEDICAL DEVICES AND METHODS OF MAKING AND USING SAME, the entirety of which is hereby incorporated by reference herein and made a part of this specification.

After immersion in the polymer solution, the substrate, now possessing a polymer layer either directly bound to the substrate, the optional silane layer, or both, may be heated at a temperature from about 60° C. to about 100° C., in embodiments from about 70° C. to about 90° C., in embodiments about 80° C. Heating may occur for a time from about 15 minutes to about 45 minutes, or more than 45 minutes, in embodiments from about 20 minutes to about 35 minutes, in embodiments about 30 minutes.

After heating, the device may again be washed. For example, the device may be subjected to sonication and cleaned with water, ethanol, methanol, isopropyl alcohol, n-butanol, dimethylformamide (DMF), dimethyl sulfoxide (DMSO), ethyl acetate, PM acetate, toluene, chloroform, dichloromethane, toluene, combinations thereof, and the like. Sonication may occur for a period of time from about 1 minute to about 10 minutes, or more than 10 minutes, in embodiments from about 2 minutes to about 8 minutes, in embodiments about 5 minutes. Sonication may occur at room temperature.

After this cleaning, the device may be rinsed with a suitable material, such as water, methanol, isopropyl alcohol, n-butanol, dimethylformamide (DMF), dimethyl sulfoxide (DMSO), ethyl acetate, PM acetate, toluene, chloroform, dichloromethane, combinations thereof, and the like. The device may then be heated at a temperature from about 60° C. to about 100° C., in embodiments from about 70° C. to about 90° C., in embodiments about 80° C. Heating may occur for a time from about 5 minutes to about 25 minutes, or more than 25 minutes, in embodiments from about 10 minutes to about 20 minutes, in embodiments about 15 minutes.

Upon completion of this heating step, the device is now ready for packaging in any material suitable for use in packaging medical devices.

The polymer layer on the resulting medical device may have a thickness less than about 2000 nanometers, in embodiments less than about 1000 nanometers, in embodiments less than about 500 nanometers, in embodiments less than about 250 nanometers, in embodiments less than about 100 nanometers, in embodiments less than about 50 nanometers, in embodiments less than about 25 nanometers, in embodiments less than about 10 nanometers, in embodiments from about 1 nanometer to about 100 nanometers, in embodiments from about 1 nanometer to about 50 nanometers, in embodiments from about 1 nanometer to about 25 nanometers, in embodiments from about 1 nanometer to about 10 nanometers. In embodiments, the polymer layer is the outermost layer of, and/or forms the outer surface of, the medical device and/or any components forming the device, e.g., filaments forming a stent.

As noted above, bioactive agents may be added to a medical device of the present disclosure, either as part of the device, and/or as part of the layer(s) applied in accordance with the present disclosure. A "bioactive agent," as used herein, includes any substance or mixture of substances that provides a therapeutic or prophylactic effect; a compound that affects or participates in tissue growth, cell growth and/or cell differentiation; a compound that may be able to invoke or prevent a biological action such as an immune response; or a compound that could play any other role in one or more biological processes. A variety of bioactive agents may be incorporated into the medical device. Moreover, any agent which may enhance tissue repair, limit the risk of restenosis, and modulate the mechanical or physical properties of the medical device, such as a stent, may be added during the preparation of the medical device. In embodiments, the bioactive agent may be added to the polymer used to form the outer layer of the medical device.

Examples of classes of bioactive agents which may be utilized in accordance with the present disclosure include antimicrobials, analgesics, anesthetics, antihistamines, anti-inflammatories, cardiovascular drugs, diagnostic agents, sympathomimetics, cholinomimetics, antimuscarinics, anti-spasmodics, hormones, growth factors, muscle relaxants, adrenergic neuron blockers, antineoplastics, immunogenic agents, immunosuppressants, steroids, lipids, lipopolysaccharides, polysaccharides, and enzymes. It is also intended that combinations of bioactive agents may be used.

Other bioactive agents which may be in the present disclosure include antirestenotic agents, including paclitaxel, paclitaxel derivatives, rapamycin, everolimus, sirolimus, taxane QP-2, actinomycin D, vincristine, methotrexate, angiopeptin, mitomycin, BCP 678, C-myc antisense, sirolimus derivatives, tacrolimus, everolimus, ABT-578, biolimus A9, tranilast, dexamethasone, methylprednisolone, interferon, leflunomide, cyclosporin, halofuginone, C-proteinase inhibitors, metalloproteinase inhibitors, batimastat, propyl hydroxylase inhibitors, VEGF, 17-β-estradiol, BCP 671, HMG CoA reductase inhibitors, combinations thereof, and the like.

Yet other bioactive agents include sympathomimetic agents; vitamins; anticholinergic agents (e.g., oxybutynin); cardiovascular agents such as coronary vasodilators and nitroglycerin; alkaloids; analgesics; non-narcotics such as salicylates, aspirin, acetaminophen, d-propoxyphene and the like; anti-cancer agents; anti-inflammatory agents such as hormonal agents, hydrocortisone, prednisolone, prednisone, non-hormonal agents, allopurinol, indomethacin, phenylbutazone and the like; prostaglandins and cytotoxic drugs; antibacterials; antibiotics; anti-fungals; anti-virals; anticoagulants; and immunological agents.

Other examples of suitable bioactive agents which may be included in the present disclosure include: viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons (β-IFN, (α-IFN and γ-IFN)); erythropoietin; nucleases; tumor necrosis factor; colony stimulating factors (e.g., GCSF, GM-CSF, MCSF); insulin; anti-tumor agents and tumor suppressors; blood proteins; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); protein inhibitors; protein antagonists; protein agonists; nucleic acids such as antisense molecules, DNA, and RNA; oligonucleotides; and ribozymes.

Suitable medical devices which may be prepared in accordance with the present disclosure include, but are not limited to, stents, filters, stent coatings, grafts, catheters, stent/grafts, clips and other fasteners, staples, sutures, pins, screws, prosthetic devices, drug delivery devices, anastomosis rings, surgical blades, contact lenses, intraocular lenses, surgical meshes, knotless wound closures, sealants, adhesives, intraocular lenses, anti-adhesion devices, anchors, tunnels, bone fillers, synthetic tendons, synthetic ligaments, tissue scaffolds, stapling devices, buttresses, lap-bands, orthopedic hardware, pacers, pacemakers, and other implants and implantable devices.

In embodiments, most of the accessible surfaces of the substrate may be covered with the polymer layer and optional silane layer. In yet other embodiments, the entire substrate is covered. The layers may cover from about 1% to about 100% of the area of the substrate, in embodiments a stent, in embodiments from about 20% to about 90% of the area of the substrate.

As noted above, in embodiments, the medical device in accordance with the present disclosure is a stent. Any stent may be treated in accordance with the methods herein. The stent may be a braided stent or other form of stent such as a laser-cut stent, stent, balloon expandable stent, self-expanding stent, knitted stent, and the like.

In embodiments, a braided vascular device such as a stent is braided from filaments which are formed from metal alloys and/or other high-temperature materials. The resulting braid is then heat-treated or "heat-set" at high temperature in order to reduce internal stresses in the filaments and/or increase or impart a self-expanding capability of the stent. Filaments making up the tubular body of a stent that has been heat set are in their least-stressed or a reduced-stressed state when the stent is in the configuration it was in during heat setting. Such a least-stressed or reduced-stressed state can include an expanded or fully expanded state.

The stent can optionally be configured to act as a "flow diverter" device for treatment of aneurysms, such as those found in blood vessels including arteries in the brain or within the cranium, or in other locations in the body such as peripheral arteries. The stent can, in embodiments, include those sold as PIPELINE™ Embolization Devices by Covidien, Mansfield, Mass. Such devices also include those disclosed in U.S. Pat. No. 8,267,986, issued Sep. 18, 2012, titled VASCULAR STENTING FOR ANEURYSMS, the entire disclosure of which is incorporated by reference herein.

For example, in accordance with the present disclosure, a device having a flow diverting section can have pores with a "flow diverting pore size." A "flow diverting pore size" can refer to pores having an average pore size (in at least a section of a device) that is sufficiently small to interfere with or inhibit fluid exchange through the pores of that section. For example, a device (e.g., stent) can have an active section or a flow diverting section with a flow diverting pore size when the pores of the section are sized to inhibit flow of blood through the sidewall into an aneurysm to a degree sufficient to lead to thrombosis and healing of the aneurysm when the device/stent is positioned in a blood vessel and adjacent to or across the neck of the aneurysm.

For example, a flow diverting pore size can be achieved when pores in the flow diverting or active section (or in the stent as a whole) have an average pore size of less than about 500 microns when the device (e.g., stent) is in the expanded state. (When "expanded state" is used herein to specify braided stent parameters such as pore sizes, the expanded state is one that the stent will self-expand to without any external expansive forces applied, and without any external longitudinal stretching or compressive forces applied. For simplicity of measurement, this expanded state can be one that the stent will self-expand to within a straight glass cylindrical tube with an inside diameter that is smaller than the maximum diameter to which the stent will self-expand in the absence of any containment or external forces.) In some embodiments, the average pore size can be less than about 320 microns. Some embodiments disclosed herein enable and provide a device and methods of manufacturing in which the device has a flow diverting section or flow diverting sidewall that has reduced thrombogenicity, or in which the device as a whole possesses flow diverting properties and reduced thrombogenicity.

Accordingly, some embodiments provide a device, such as a braided stent, that can have a flow diverting section or other portion of the device that provides embolic properties so as to interfere with blood flow in (or into) the body space (e.g., an aneurysm) in (or across) which the device is deployed. The porosity and/or pore size of one or more sections of the device can be selected to interfere with blood flow to a degree sufficient to thrombose the aneurysm or other body space.

For example, some embodiments provide a device (e.g., stent) that can be configured to interfere with blood flow to generally reduce the exchange of blood between the parent vessel and an aneurysm, which can induce thrombosis of the aneurysm. A device (or a device component, such as a sidewall of a stent or a section of such a sidewall) that thus interferes with blood flow can be said to have a "flow diverting" property.

Additionally, in some embodiments, a device (e.g., stent) can be provided with a porosity in the range of 5%-95% may be employed in the expanded braid. In some embodiments, a porosity in the range of 30%-90% may be employed. Further, a porosity in the range of 50%-85% may be employed. The porosity can be computed as the percentage of the total outer surface area of the stent that is open, wherein the total outer surface area is the sum of the open (pore-occupied) surface area and the solid (filament-occupied) surface area.

Further, in some embodiments, a device (e.g., stent) can be provided with a pore size from about 20 to about 300 microns (inscribed diameter). In some embodiments, a pore size from about 25 to about 250 microns (inscribed diameter) may be employed. In some embodiments, a pore size from about 50 to about 200 microns (inscribed diameter) may be employed.

Methods of treatment and methods of manufacturing embodiments of the devices (e.g., stents) disclosed herein are also provided.

Some embodiments of processes disclosed herein include mounting or maintaining a braided device (e.g., stent) in a longitudinally stretched configuration during the process of applying the polymer layer and any optional silane layer. Such a device can have an expanded configuration in which the pores thereof are generally circumferentially elongated, which results in a decreased pore size or a relatively "closed" configuration. In contrast, the pore size is increased or in a relatively "open" configuration when the device is in the longitudinally stretched configuration. In the longitudinally stretched configuration, many, if not all, of the pores of the device can be opened to an enlarged pore size, or to a generally maximum pore size.

For example, in some embodiments, the longitudinally stretched configuration can open the pores by orienting the individual filaments of the device to create a pattern of open-pore quadrilaterals, such as squares, rectangles, parallelograms, rhombuses, trapezoids, etc., which can allow the pore size to be generally maximized. Further, the quadrilaterals can be formed by filaments that cross at angles from about 0° to about 15° from a right angle. In some embodiments, the angles can be from about 0° to about 10° from a right angle. In some embodiments, the angles can be from about 0° to about 5° from a right angle. Additionally, in some embodiments, the filaments can form right-angled quadrilaterals, such as squares and rectangles, which allows the pore size to be maximized. However, not every pore shape circumscribed by the filaments may be a right-angled quadrilateral, and some variation between pores in the same or different sections of a device is possible.

In embodiments, the device (e.g., stent) can take the form of a vascular occluding device, a revascularization device, and/or an embolization device. In some embodiments, the device can be an expandable stent made of two or more filaments. The filaments can be formed of known flexible materials including platinum, cobalt, chromium, nickel, alloys thereof, and combinations thereof. In some embodiments, the filaments can be wire having a generally circular, round or ovoid cross-section. Further, the filaments can be configured such that the device is self-expanding. In some embodiments, the device can be fabricated from a first group of filaments made of platinum alloyed with tungsten (e.g., about 8% tungsten), and a second group of filaments made of cobalt-chromium alloy or cobalt-nickel alloy (e.g., 35N LT™). In other embodiments, one or more of the filaments can be formed of a biocompatible metal material or a biocompatible polymer.

The wires or filaments can be braided into a resulting tubular, lattice-like structure. In at least one embodiment, during braiding or winding of the device (e.g., stent), the filaments can be braided using a 1-over-2-under-2 pattern. In other embodiments, however, other methods of braiding can be followed, without departing from the scope of the disclosure. The device can exhibit a porosity configured to reduce hemodynamic flow into and/or induce thrombosis within, for example, an aneurysm, but simultaneously allow perfusion to an adjacent branch vessel whose ostium is crossed by a portion of the device. As will be appreciated, the porosity of the device can be adjusted by "packing" the device during deployment, as known in the art. The ends of the device can be cut to length and therefore remain free for radial expansion and contraction. The device can exhibit a high degree of flexibility due to the materials used, the density of the filaments, and the fact that the ends of the wires or filaments are not secured to each other.

In addition to the methods described above, in embodiments, combinations of filaments of the present disclosure may have different polymer layer applied thereto. For example, in embodiments, a medical device of the present disclosure may include platinum or platinum alloy filaments braided with or combined with cobalt-nickel or cobalt-chromium alloy filaments. The platinum or platinum alloy filaments may possess a layer of phosphorylcholine (e.g. with no intervening layers between the filament and the phosphorylcholine), while the cobalt-nickel or cobalt-chromium alloy filaments may possess a silane intermediate layer between the alloy filaments and an outer layer of phosphorylcholine. In such cases, the phosphorylcholine may directly bind to the platinum or platinum alloy filaments by covalent bonding, chemical bonding, combinations thereof, and the like. Similarly, the phosphorylcholine may be chemically bonded to a silane layer over the cobalt-nickel or cobalt-chromium alloy filaments, or the phosphorylcholine may be covalently bonded to a silane layer over the cobalt-nickel or cobalt-chromium alloy filaments.

Other combinations are also contemplated. For example, a platinum or platinum alloy filament may also possess an intermediate silane layer in addition to an outer phosphorylcholine layer, while a cobalt-nickel or cobalt-chromium alloy filament may possess an outer phosphorylcholine layer but no intermediate silane layer.

FIG. 1 illustrates a tubular, self-expanding device, shown as a stent 100, including a polymer layer 110 disposed along at least a portion thereof. An optional silane layer (not shown) may be between the filaments used to form the stent 100 and polymer layer 110. The tubular stent 100 includes an elongate hollow body which can be formed from a plurality of braided filaments as discussed herein. Some embodiments disclosed herein can include a polymer layer along the entire length of the stent or merely along only a portion thereof. The stent 100 can include a flow diverting portion 112. The flow diverting portion 112 can include a plurality of pores that have a flow diverting pore size; instead of or in addition to this property, the flow diverting portion 112 can have a flow diverting porosity. The flow diverting portion 112 can include a portion of the stent 100, or the entire stent. The flow diverting pore size can be an average pore size within a relevant portion of the stent, e.g. within the flow diverting portion 112 or a portion thereof, or a "computed" pore size, one that is computed from measured or nominal basic stent parameters such as braid angle, number of filaments, filament size, filament diameter, stent diameter, longitudinal picks per inch, radial picks per inch, etc. Such a computed pore size can be considered to be one type of average pore size. The flow diverting pore size can have a size that interferes with or inhibits blood flow through the sidewall of the stent 100, for example, between the parent vessel and an aneurysm sufficient to induce or lead to thrombosis of the aneurysm. The layer can be disposed partially or entirely along the flow diverting portion 112, or along another portion of the stent 100.

In some embodiments, the pores of the flow diverting portion 112 can have an average pore size of less than 500 microns (inscribed diameter), or from about 20 to about 300 microns (inscribed diameter). Further, the average pore size can be from about 25 to about 250 microns (inscribed diameter). Furthermore, the average pore size can be from about 50 to about 200 microns (inscribed diameter).

The average pore size of the pores in the flow diverting portion 112 can be the average size of the pores measured with or without layer materials disposed thereon. Thus, the average pore size of the flow diverting portion of a bare stent can be within the flow diverting ranges. Further, the average pore size of the flow diverting portion of a stent can be within the flow diverting ranges. Furthermore, the flow diverting portion 112 can possess pores having sizes above or below the range of the average pore size.

Figure 2A:
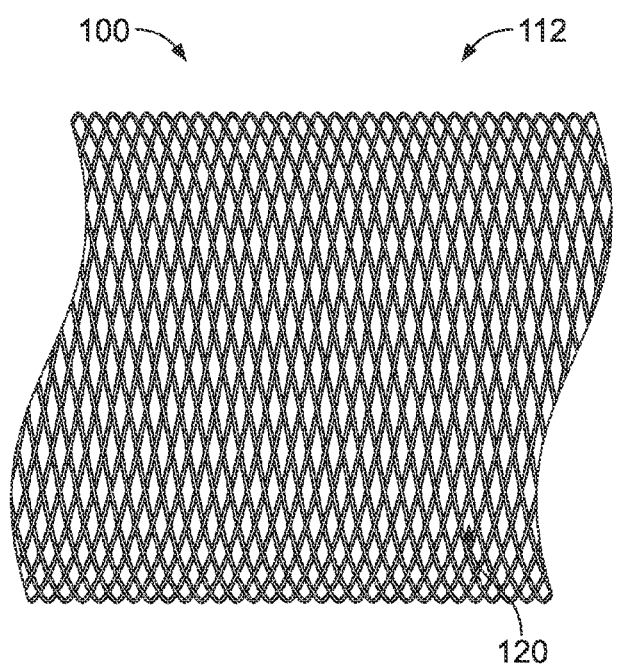
FIG. 2A is an enlarged view of the stent shown in FIG. 1, according to some embodiments.

FIG. 2A illustrates an enlarged view of a section of the flow diverting portion 112 of the stent 100. In this embodiment, the flow diverting portion 112 includes a plurality of filaments 120 that are braided together to form the tubular body of the stent 100. FIG. 2A illustrates the self-expanding stent 100 in an expanded or relaxed state. In this expanded or relaxed state, the filaments 120 cross each other to form the pores of the stent 100.

Figure 2B:
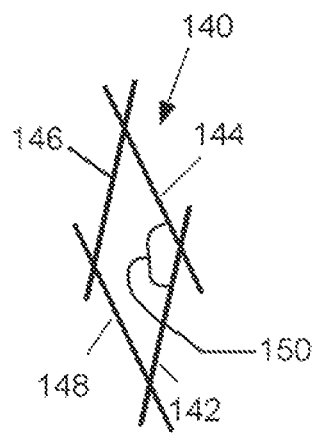
FIGS. 2B-2C are detail views of a pore of the stent of FIG. 1, in various conditions.

FIG. 2B illustrates a single pore 140 of the flow diverting section 112 when in the relaxed state. The pore 140 is formed by a plurality of filaments 142, 144, 146, and 148. As shown, the filaments 142, 144 cross each other to form an obtuse angle 150. In some embodiments, the obtuse angle 150 can be from about 110° to about 170°. Further, the obtuse angle 150 can be from about 120° to about 165°. Further, the obtuse angle 150 can be from about 130° to about 160°, and in some embodiments, the obtuse angle 150 can be about 150°.

Figure 2C:
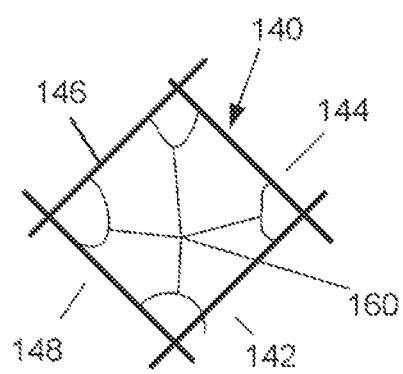

Accordingly, the size or configuration of the pore 140 is "closed" or relatively small in the expanded or relaxed state shown in FIG. 2B when compared with the relatively "open" size of the pore 140 when the stent 100 is in a longitudinally stretched configuration, as shown in FIG. 2C. FIG. 2C illustrates that the filaments 142, 144, 146, and 148 each cross each other at angles 160 that approximate a right angle, e.g. within from about 0° to about 15° from a right angle. In some embodiments, the angles 160 can be from about 0° to about 10° from a right angle. In some embodiments, the angles 160 can be from about 0° to about 5° from a right angle.

As noted above, filaments 142, 144, 146 and 148 may be made of different materials having different layers thereon. For example, at least one of filaments 142, 144, 146 and 148 may be formed of a cobalt-nickel or cobalt-chromium alloy having both a silane layer and outer polymer layer applied thereto (not shown), while at least one of the other filaments may be formed of a platinum or platinum alloy filament having a polymer layer but no intermediate silane layer (not shown).

Additionally, in order to maximize the pore size, in some embodiments, the filaments can form right-angled quadrilaterals, such as squares and/or rectangles. However, not every pore shape circumscribed by the filaments may be a right-angled quadrilateral, and some variation between pores in the same or different sections of a stent is possible.

A device can be prepared according to some embodiments by braiding a plurality of filaments to form a braided stent, filter, or other braided device. The device can then be cleaned and heat treated, if necessary, to impart desired characteristics to the device. Thereafter, the device can have layers applied thereto using aspects of the methods disclosed herein.

Some embodiments of the devices and methods disclosed herein can therefore provide a device, such as a stent or a braided stent, having an outer layer that has low or no thrombogenicity, that also has a flow diverting pore size and/or a flow diverting porosity that is/are exhibited throughout the entire stent, or in a flow diverting portion or section of the stent.

The antithrombogenic polymer layer of the present disclosure reduces the thrombogenicity of the stent, device, section, etc., having the polymer layer as compared to a similar stent, device, section, etc., lacking the polymer layer. The reduction in thrombogenicity can be significant. Stents possessing layers according to the present disclosure have been tested for increased antithrombogenicity via thrombogram, in which thrombin formation is measured by detecting the fluorescence of a fluorescent additive in a test solution containing a sample of the stent. The time elapsed before peak thrombin formation was observed. Stents having polymer layers in accordance with the present disclosure were found to result in a significant delay in peak thrombin formation, as compared to a similar stent which did not possess the polymer layer. In particular, the elapsed time before peak thrombin formation was found to be about 4 times that of the similar stent lacking the polymer layer. Accordingly, the time before peak thrombin formation with the device, stent, section, etc. having the polymer layer can be more than 1.5 times, or more than 2 times, or more than 3 times, or about 4 times that of a similar device, stent, section, etc., lacking the polymer layer.

Stents having polymer layers in accordance with the present disclosure were found to result in a significantly longer lag phase (the elapsed time before the onset of thrombin formation), as compared to a similar stent which did not possess the polymer layer. In particular, the lag phase was found to be about 4 times that of the similar stent lacking the polymer layer. Accordingly, the lag phase with the device, stent, section, etc. having the polymer layer can be more than 1.5 times, or more than 2 times, or more than 3 times, or about 4 times that of a similar device, stent, section, etc., lacking the polymer layer.

Stents having polymer layers in accordance with the present disclosure were found to result in a significantly lower peak thrombin concentration, as compared to a similar stent which did not possess the polymer layer. In particular, the peak thrombin concentration was found to be about 0.3 times that of the similar stent lacking the polymer layer. Accordingly, the peak thrombin concentration with the device, stent, section, etc. having the polymer layer can be less than 0.8 times, or less than 0.6 times, or less than 0.5 times, or about 0.3 times that of a similar device, stent, section, etc., lacking the polymer layer.

The thickness of the layers can be less than 100 nanometers, less than 50 nanometers, less than 25 nanometers, or less than 10 nanometers, or from 1 nanometer to 10, 25, 50, or 100 nanometers. In embodiments, the thickness of the polymer layers is from about 2 to about 3 nanometers. In various embodiments of the stent, device, etc., the foregoing properties can be present singly or in any combination, or not present at all.

The processes and devices of the present disclosure have several advantages. The methods of the present disclosure, in some cases forming a silane on a medical device followed by forming a polymer layer thereon, may enhance adherence of the polymer layer to the substrate surface, thereby increasing coverage on the substrate. Medical devices having polymer layers in accordance with the present disclosure thus have both a greater area of coverage, as well as an ability to retain the outer layers and avoid delamination thereof. Moreover, use of materials like phosphorylcholines as the polymer layer provides medical devices with very low thrombogenicity.

The following Examples are being submitted to illustrate embodiments of the present disclosure. These Examples are intended to be illustrative only and are not intended to limit the scope of the present disclosure. Also, parts and percentages are by weight unless otherwise indicated. As used herein, "room temperature" refers to a temperature of from about 20° C. to about 30° C.

EXAMPLE 1

Braided tubular stents were treated as follows. Each of the stents was configured as follows: 48 braided filaments, of which 12 were of platinum alloyed with 8% tungsten, with 0.0012 inch filament diameter, 12 were of cobalt-chromium (35N LT™), with 0.0012 inch filament diameter, and 24 were of 35NLT, with 0.0014 inch filament diameter; overall outside diameter 5.2 mm and longitudinal picks per inch of 275, both dimensions prevailing when in an expanded, unconstrained and unstretched condition.

The stents were provided in their cleaned, "bare metal" condition, and prepared as follows. Each stent was hydroxylated (—OH) via acid (e.g. $HNO_3$, or a mixture of $H_2SO_4$/$H_2O_2$), hydroxide (e.g., NaOH, or a mixture of $NH_3OH$/$H_2O_2$) or plasma treatment (e.g., $H_2O$, $O_3$). The hydroxylated metal was rinsed with ethanol and deionized (DI) water, and placed into a container with a 3-Glycidoxypropyltrimethoxysilane (GPTS) solution for silanization. The GPTS was in a solution using 95%/5% by volume of ethanol/water mixture as a solvent at a concentration of GPTS of 2% by weight. The stent in solution was stirred at 130 revolutions per minute (rpm) for a period of time of about 90 minutes. The immersion and stirring process was performed under room temperature. After that, the metal was rinsed with ethanol and water, and cured at 80° C. for 15 minutes. (The temperature can be changed to 110° C. or 120° C. and the curing time can be varied from 15 minutes to 90 minutes.)

The silanized stent was then dipped into a reactive MPC solution containing amino groups (LIPIDURE®-NH01, having a concentration of 5%) for 1 minute and cured at 80° C. for at least 30 minutes. After curing, the metal surface was washed with water in sonication for 5 minutes to eliminate non-covalently bonded polymer. The washed metal surface was dried at a temperature of about 80° C. for 15 minutes. After completion of the process and trimming to length, the stents could be described as tubular braided stents, open at each end with a lumen extending from one end to the other, and with a an outer layer of MPC over the entirety of the stent filaments. The MPC was directly bonded to the platinum alloy filaments, and bonded to a silane layer over the cobalt-chromium alloy filaments.

Stents having layers applied thereto according to this Example 1 were tested for decreased thrombogenicity via thrombogram, employing the following assay. A test solution was prepared as a mixture of (a) lyophilized platelets (catalog no. 101258, Biodata Corporation, Horsham, Pa.; reconstituted with IRIS buffered saline to a pre-mixture platelet concentration of 200,000 per microliter), (b) lyophilized normal control plasma (PlasmaCon N, catalog no. 30-201, R2 Diagnostics, South Bend, Ind.; reconstituted with water), (c) fluorogenic substrate (Z-Gly-Gly-Arg-AMC-HCl, catalog no. I-1140, Bachem Americas Inc., Torrance, Calif.; pre-mixture concentration of 40 mM in dimethyl sulfoxide), and (d) calcium chloride (catalog no. 223506-2.5 KG, Sigma Aldrich, St. Louis, Mo.; pre-mixture concentration of 1M in water). These were combined in the test solution in proportions (by volume) of 1 part fluorogenic substrate to 2 parts calcium chloride to 6 parts platelets to 100 parts plasma. The final concentration of fluorogenic substrate was about 400 μM and the final concentration of calcium chloride was about 20 mM.

A calibration mixture was prepared by adding reference thrombin calibrator solution (catalog no. TS20.00, Stago Diagnostics Inc., Parsippany, N.J.) and the fluorogenic substrate to the control plasma, in proportions (by volume) of 1 part substrate to 11 parts calibrator solution to 98 parts control plasma, arriving at a final concentration of the fluorogenic substrate of about 400 μM.

Samples of stents prepared according to this Example 1 ("test stents") and of identical but bare-metal stents ("bare stents") were prepared by cutting sections of each stent to a length of 9 mm. The 9 mm sections of test stents and bare stents were placed individually in separate wells of a black, opaque 96-well polystyrene microplate (Fisher Scientific, Waltham, Mass.). Test solution (330 microliters) was added to each well containing a test stent or bare stent sample, as well as to several wells each containing a 4 mm glass sphere (Fisher Scientific, catalog no. 11-312B) to serve as a positive control, and to several empty wells to serve as a "blank" or negative control. Calibration mixture (330 microliters) was added to several empty wells (separate from the negative-control wells) to provide a calibration reference. Fluorescence was measured in a Fluoroskan ASCENT™ microplate reader (Fisher Scientific, catalog no. 5210470) with an excitation wavelength of 360 nm, emission wavelength of 460 nm, reading interval of 20 to 30 seconds, and total experimental time of 150 minutes.

The test stents were found to result in a significant delay in peak thrombin formation, as compared to the bare stents. In particular, the elapsed time before peak thrombin formation was found to be about 4 times the time observed with the bare stents (109.3 minutes for the test stents compared to 29.4 minutes for the bare stents). The test stents were also found to result in a longer lag phase, i.e., the elapsed time before the onset of thrombin formation; the observed lag phase for the test stents was about 4 times as long as that of the bare stents (99.3 minutes for the test stents compared to 26.2 minutes for the bare stents). The test stents were also found to result in lower peak thrombin concentration than the bare stents; the observed peak thrombin concentration for the test stents was about 0.3 times that of the bare stents (150.3 nM for the test stents compared to 473.6 nM for the bare stents).

The test stents were also found to be only slightly more thrombogenic than the empty (blank) polystyrene wells. In particular, the elapsed time before peak thrombin formation of the test stents was found to be about 97% of that measured for the empty wells (109.3 minutes for the test stents compared to 112.3 minutes for the empty wells). The observed lag phase for the test stents was about 97% of that of the empty wells (99.3 minutes for the test stents compared to 102.9 minutes for the empty wells). The test stents were also found to result in a peak thrombin concentration that was only about 6% higher than that of the empty wells (150.3 nM for the test stents compared to 141.9 nM for the empty wells).

The thickness of the silane layer applied to the cobalt-chromium filaments was measured to be from about 1 to about 10 nanometers, and the thickness of the MPC layer applied to the platinum-tungsten filaments, and to the cobalt-chromium filaments over the silane layer, was measured to be from about 2 to about 3 nanometers.

Methods of Treatment

As mentioned elsewhere herein, the present disclosure also includes methods of treating a vascular condition, such as an aneurysm or intracranial aneurysm, with any of the embodiments of the stents disclosed herein. The low-thrombogenicity stents of the present disclosure can, in some embodiments, be deployed across the neck of an aneurysm and the flow-diverting properties employed to reduce blood flow between the aneurysm and the parent vessel, cause the blood inside the aneurysm to thrombose and lead to healing of the aneurysm.

Significantly, the low-thrombogenicity stents disclosed herein can facilitate treatment of a large population of patients for whom flow-diverter therapy has not been previously possible. Such patients are those who have previously suffered from a hemorrhagic aneurysm or who have been diagnosed as being at risk for hemorrhage from an aneurysm in the intracranial arterial system. These patients cannot currently be treated with commercially available flow-diverting stents because those stents are bare metal, braided stents whose implantation requires the patient to take anti-platelet medication (typically aspirin and PLAVIX™ (clopidogrel)) for a long period of time following implantation. The purpose of the anti-platelet medication is to counteract the tendency of the bare-metal stent to cause thrombus (blood clots) to form in the patient's vasculature. However, for a patient who has suffered from or is at risk of intracranial hemorrhage, taking the anti-platelet medication can cause, or put the patient at higher risk of, such a hemorrhage. Low-thrombogenicity flow-diverting stents, such as some embodiments of the stents disclosed herein, can make flow-diverter therapy possible for patients who cannot tolerate anti-platelet medication because the reduced thrombogenicity can reduce or eliminate the need for blood thinners.

In order to implant any of the stents disclosed herein, the stent can be mounted in a delivery system. Suitable delivery systems are disclosed in U.S. patent application Ser. No. 14/040,477, filed Sep. 27, 2013, titled DELIVERY OF MEDICAL DEVICES; U.S. Patent Application Publication No. 2013/0226276, published Aug. 29, 2013, titled METHODS AND APPARATUS FOR LUMINAL STENTING; and in U.S. Pat. No. 8,273,101, issued Sep. 25, 2012, titled SYSTEM AND METHOD FOR DELIVERING AND DEPLOYING AN OCCLUDING DEVICE WITHIN A VESSEL. The entire disclosures of both of these documents are incorporated by reference herein and made a part of this specification. In particular, these documents' teachings regarding stent delivery systems and methods may be employed to deliver any of the stents disclosed herein in the same manner, to the same bodily location(s), and using the same components as are disclosed in these incorporated documents.

Generally, the delivery system can include an elongate core assembly having a distal segment that supports or contains the stent, and both components can be slidably received in a lumen of a microcatheter or other elongate sheath for delivery to any region to which the distal opening of the microcatheter can be advanced. The core assembly is employed to advance the stent through the microcatheter and out the distal end of the microcatheter so that the stent is allowed to self-expand into place in the blood vessel, across an aneurysm or other treatment location.

A treatment procedure can begin with obtaining percutaneous access to the patient's arterial system, typically via a major blood vessel in a leg or arm. A guidewire can be placed through the percutaneous access point and advanced to the treatment location, which can be in an intracranial artery. The microcatheter is then advanced over the guidewire to the treatment location and situated so that a distal open end of the catheter is adjacent to the treatment location. The guidewire can then be withdrawn from the microcatheter and the core assembly, together with the stent mounted thereon or supported thereby, can be advanced through the microcatheter and out the distal end thereof. The stent can then self-expand into apposition with the inner wall of the blood vessel. Where an aneurysm is being treated, the stent is placed across the neck of the aneurysm so that a sidewall of the stent (e.g. a section of the braided tube) separates the interior of the aneurysm from the lumen of the parent artery. Once the stent has been placed, the core assembly and microcatheter are removed from the patient. The stent sidewall can now perform a flow-diverting function on the aneurysm, thrombosing the blood in the aneurysm and leading to healing of the aneurysm.

Because of the low-thrombogenic properties of the stents disclosed herein, certain additional aspects of the methods of treatment are possible. For example, the patient can be one who has previously suffered from, or who has been diagnosed as being at risk of, hemorrhage from an aneurysm in arterial anatomy such as the intracranial arterial system. The patient may have been diagnosed as being at risk for an intracranial hemorrhage, a cerebral hemorrhage from an aneurysm, etc. The patient can be prescribed a reduced regimen of anti-platelet medication as compared to the regimen or protocol that would be necessary for a patient who received an otherwise similar stent that lacked the phosphorylcholine outer layer or surface. The regimen can be "reduced" in the sense that the patient takes a lower dosage, fewer medications, less powerful medications, follows a lower dosage frequency, and/or takes medication for a shorter period of time following implantation of the stent, or otherwise. Alternatively, the patient may be prescribed no blood thinning medication at all.

The devices and methods discussed herein are not limited to the application of layers on stents, but may include any number of other implantable devices. Treatment sites may include blood vessels and areas or regions of the body such as organ bodies.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable by different embodiments of the disclosure in order to be encompassed within the scope of the disclosure.

What is claimed is:

1. A medical device, comprising:
an expandable tubular body comprising a plurality of braided filaments configured to be implanted in a blood vessel, the plurality of braided filaments comprising:
a first filament comprising platinum or platinum alloy and a first coating comprising a first phosphorylcholine applied directly on the first filament; and
a second filament comprising cobalt-chromium alloy, a second coating comprising a second phosphorylcholine, and a silane layer between the second filament and the second coating;
wherein the first and second coatings each define a thickness of less than 100 nanometers; and
wherein the silane layer comprises a silane selected from the group consisting of 3-glycidoxypropyltrimethoxysilane, 2-(3,4-epoxycyclohexyl)ethyltriethoxysilane, 2-(3,4-epoxycyclohexyl)ethyl-trimethoxysilane, (3-glycidoxypropyl)trimethoxysilane, (3-glycidoxypropyl)triethoxysilane, 5,6-epoxyhexyltriethoxysilane, (3-glycidoxypropyl)methyldiethoxysilane, (3-glycidoxypropyl)methyldimethoxysilane, (3-glycidoxypropyl)dimethylethoxysilane, 3-isocyanatopropyltriethoxysilane, (isocyanatomethyl)methyldimethoxysilane, 3-isocyanatopropyltrimethoxysilane, tris(3-trimethoxysilylpropyl)isocyanurate, (3-triethoxysilylpropyl)-t-butylcarbamate, triethoxysilylpropylethylcarbamate, 3-thiocyanatopropyltriethoxysilane, and combinations thereof.

2. The medical device of claim 1, wherein the first and second phosphorylcholines are selected from the group consisting of 2-methacryloyloxyethyl phosphorylcholine, 2-acryloyloxyethyl phosphorylcholine, and phosphorylcholines based upon monomers including 2-(meth)acryloyloxyethyl-2'-(trimethylammonio)ethyl phosphate, 3-(meth)acryloyloxypropyl-2'-(trimethylammonio)ethyl phosphate, 4-(meth)acryloyloxybutyl-2'-(trimethylammonio)ethyl phosphate, 5-(meth)acryloyloxypentyl-2'-(trimethylammonio)ethyl phosphate, 6-(meth)acryloyloxyhexyl-2'-(trimethylammonio)ethyl phosphate, 2-(meth)acryloyloxyethyl-2'-(triethylammonio)ethyl phosphate, 2-(meth)acryloyloxyethyl-2'-(tripropylammonio)ethyl phosphate, 2-(meth)acryloyloxyethyl-2'-(tributylammonio)ethyl phosphate, 2-(meth)acryloyloxypropyl-2'-(trimethylammonio)ethyl phosphate, 2-(meth)acryloyloxybutyl-2'-(trimethylammonio)ethyl phosphate, 2-(meth)acryloyloxypentyl-2'-(trimethylammonio)ethyl phosphate, 2-(meth)acryloyloxyhexyl-2'-(trimethylammonio)ethyl phosphate, 2-(meth)acryloyloxyethyl-3'-(trimethylammonio)propyl phosphate, 3-(meth)acryloyloxypropyl-3'-(trimethylammonio)propyl phosphate, 4-(meth)acryloyloxybutyl-3'-(trimethylammonio)propyl phosphate, 5-(meth)acryloyloxypentyl-3'-(trimethylammonio)propyl phosphate, 6-(meth)acryloyloxyhexyl-3'-(trimethylammonio)propyl phosphate, 2-(meth)acryloyloxyethyl-4'-(trimethylammonio)butyl phosphate, 3-(meth)acryloyloxypropyl-4'-(trimethylammonio)butyl phosphate, 4-(meth)acryloyloxybutyl-4'-(trimethylammonio)butyl phosphate, 5-(meth)acryloyloxypentyl-4'-(trimethylammonio)butyl phosphate, 6-(meth)acryloyloxyhexyl-4'-(trimethylammonio)butyl-phosphate, and combinations thereof.

3. The medical device of claim 1, wherein the first and second phosphorylcholines comprise a copolymer having a reactive chemical group.

4. The medical device of claim 3, wherein the reactive chemical group is selected from the group consisting of amine, hydroxyl, epoxy, silane, aldehyde, carboxylate and thiol.

5. The medical device of claim 1, wherein the silane layer comprises 3-glycidoxypropyltrimethoxysilane.

6. The medical device of claim 1, wherein the first phosphorylcholine, or a polymer or copolymer thereof, is chemically bonded directly to the first filament.

7. The medical device of claim 1, wherein the first phosphorylcholine, or a polymer or copolymer thereof, is covalently bonded to the first filament.

8. The medical device of claim 1, wherein the second phosphorylcholine, or a polymer or copolymer thereof, is covalently bonded to the silane layer on the second filament.

9. The medical device of claim 1, wherein the expandable tubular body has a sidewall formed by the plurality of braided filaments, the sidewall having a plurality of pores therein, the plurality of pores being sized to inhibit flow of blood through the sidewall into an aneurysm to a degree sufficient to lead to thrombosis and healing of the aneurysm when the expandable tubular body is positioned in a blood vessel and adjacent to the aneurysm.

10. The medical device of claim 1, wherein the expandable tubular body has a sidewall formed by the plurality of braided filaments, the sidewall having a plurality of pores therein, the plurality of pores having an average pore size that is less than or equal to 500 microns.

11. The medical device of claim 1, wherein the expandable tubular body is heat set so that the plurality of braided filaments are at their least-stressed configuration in the expandable tubular body.

12. The medical device of claim 1, wherein the first and second coatings form an outermost surface of the respective first and second filaments.

13. The medical device of claim 1, wherein the medical device comprises a stent.

14. The medical device of claim 1, wherein the expandable tubular body is self-expanding.

15. The medical device of claim 1, wherein the medical device is less thrombogenic than an identical device whose braided filaments are entirely bare metal.

16. The medical device of claim 1, wherein the medical device exhibits an elapsed time before peak thrombin formation that is at least 1.5 times the elapsed time before peak thrombin formation for an identical device whose braided filaments are entirely bare metal.

17. The medical device of claim 1, wherein the medical device exhibits a peak thrombin concentration that is less than 0.8 times the peak thrombin concentration for an identical device whose braided filaments are entirely bare metal.

18. The medical device of claim 1, wherein the first and second coatings each define a thickness from about 1 nanometer to about 25 nanometers.

19. The medical device of claim 1, wherein the first and second coatings each define a thickness from about 1 nanometer to about 10 nanometers.

* * * * *